United States Patent [19]
Brown et al.

[11] Patent Number: 5,350,080
[45] Date of Patent: Sep. 27, 1994

[54] MULTI-ACCESS PORT FOR USE IN A CELL CULTURE MEDIA SYSTEM

[75] Inventors: Dennis Brown, Logan; Dale G. Kern, Hyde Park, both of Utah

[73] Assignee: HyClone Laboratories, Logan, Utah

[21] Appl. No.: 37,940

[22] Filed: Mar. 26, 1993

Related U.S. Application Data

[63] Continuation-in-part of Ser. No. 15,804, Feb. 10, 1993.

[51] Int. Cl.5 ............................................. B65D 47/00
[52] U.S. Cl. ..................................... 220/465; 215/247; 383/66; 604/408
[58] Field of Search ............... 435/284, 296, 311, 810; 220/465, 254; 215/247; 383/66; 604/408, 415

[56] References Cited

U.S. PATENT DOCUMENTS

| | | | |
|---|---|---|---|
| 3,108,732 | 10/1963 | Curie et al. | 383/66 X |
| 3,230,954 | 1/1966 | Burgess et al. | 215/247 X |
| 3,870,183 | 3/1975 | Luczkiw | 215/247 |
| 4,000,829 | 1/1977 | Johnson, Jr. et al. | 215/247 X |
| 4,049,033 | 9/1977 | Ralston, Jr. | 105/5 |
| 4,150,673 | 4/1979 | Watt | 128/272 |
| 4,307,766 | 12/1981 | Tanokura | 150/8 |
| 4,445,550 | 5/1984 | Davis et al. | 220/465 X |
| 4,523,691 | 6/1985 | Larkin et al. | 220/266 |
| 4,524,880 | 6/1985 | Danielson et al. | 604/415 X |
| 4,838,875 | 6/1989 | Somor | 604/408 X |
| 4,910,147 | 3/1990 | Bacehowski et al. | 435/296 |
| 5,069,370 | 12/1991 | Cady et al. | 222/464 |
| 5,083,686 | 1/1992 | Cady et al. | 222/464 |
| 5,160,333 | 11/1992 | Wells | 604/408 |
| 5,207,638 | 5/1993 | Choksi et al. | 604/408 X |

*Primary Examiner*—Steven M. Pollard
*Attorney, Agent, or Firm*—Workman, Nydegger & Jensen

[57] ABSTRACT

A multi-access port is provided having a mounting flange, an access cap, and a sidewall extending from the mounting flange to the access cap. Apertures are formed in the access cap in which are fitted tubing connectors having a lower tip extending below the access cap a distance less than the distance between the mounting flange and the access cap and having an upper tip extending above the access cap. A bottom surface of the mounting flange has formed therein channels capable of providing liquid communication therethrough when the bottom surface of the mounting flange is blocked or otherwise obscured by the bottom of the media bag in which the port is affixed. The multi-access port is typically mounted in the wall of a media bag such as media bags used in cell culture media containment system. The cell culture media containment system of the present invention comprises a mixing bag having walls forming a mixing chamber therein, a storage bag having walls forming a storage chamber therein, the storage bag substantially enclosing mixing bag, with a multi-access port affixed through the walls of both the storage bag and the mixing bag to provide access to the mixing chamber. A multi-access port is also utilized within the wall of the storage bag to provide access thereto when dispensing media stored in the storage bag.

11 Claims, 7 Drawing Sheets

MULTI-ACCESS PORT FOR USE IN A CELL CULTURE MEDIA SYSTEM

BACKGROUND OF THE INVENTION

1. Related Applications

This application is a continuation-in-part of U.S. application Ser. No. 08/015,804 filed on Feb. 10, 1993 for SYSTEM AND METHODS FOR STORING, RECONSTITUTING, DISPENSING, AND HARVESTING CELL CULTURE MEDIA with Dale Kern as the named inventor.

2. Field of the Invention

The present invention relates generally to a port for use in a liquid dispensing system. More particularly, the present invention relates to a port for use in a cell culture media reconstituting, dispensing and/or harvesting system.

3. Background Technology

Cell culture media is in increasing demand by scientists and technicians working in the biotechnology sciences. Scientists and technicians often require the use of cell culture media for use in propagating cell and tissue cultures. Cell culture media is typically a solution of amino acids, electrolytes, serum, serum fractions, vitamins, and growth factors. Constituents of cell culture media are combined in quantities to adjust the pH, osmolarity, and other essential parameters for consistent and rapid cell growth therein.

Cell culture media provide an environment in which cells may exist and either develop within themselves a desired cellular product during growth or secrete the desired protein or cellular product into the surrounding medium as a byproduct of growth. Those cells that develop the desired cellular product within their structures must be chemically or mechanically fragmented in order to harvest the desired protein. More complex cells, such as mammalian cells, can produce sugar-modified proteins and secrete the desired glycoprotein or other cellular product into the cell culture medium for easy collection.

Cell culture media is typically sold in either a liquid or a powdered form. The advantages to the liquid form are that sterile liquid cell culture media may be immediately introduced into the bioreactor in which the cells will grow. The disadvantages of liquid media, however, are that liquid media is less stable during shipment and storage and, therefore, requires tighter inventory control. Typically, liquid media must also be stored in a refrigerated environment and because of its relatively high weight when compared to powdered cell culture media, shipping is more expensive.

As a result of the increased costs and risks involved in shipping and storing liquid cell culture media, users of larger quantities of cell culture media generally purchase the media in a powdered form. This powdered form requires less storage space, is easier to ship, and remains stable over a longer period of time.

Powdered media necessitates the use of equipment to reconstitute the powdered cell culture media into a liquid form prior to introduction into the cell growth container. Powdered cell culture media is typically reconstituted by mixing the powdered cell culture media and water for injection in a container. During mixing, it is not uncommon for powdered cell culture media to become airborne and be distributed throughout the environment surrounding the mixing area. Spillage may also occur. After mixing of the water and powder, the reconstituted cell culture media is then processed through one of the known sterilization techniques prior to introduction into the bioreactor. As a result, all of the components utilized in the reconstitution of powdered cell culture media must be capable of undergoing sterilization through one of the known methods, the most preferable being gamma irradiation sterilization. In addition, most components requiring rigidity will be constructed of high density polyethylene.

Some reconstitution or dispensing systems utilize a large plastic barrel having a volumetric capacity sufficient to contain a large quantity of cell culture media. An example of such a dispensing system utilizing a barrel is illustrated in U.S. Pat. No. 5,069,370 issued to Cady et. al. In Cady, sterilized cell culture media is dispensed through a dispensing port located within a bung hole of the barrel. A series of tubes extend both inwardly and outwardly from the port function to both dispense and supplement the liquid cell culture media contained therein.

In addition, other tubes serve to provide sampling of the liquid cell culture media and in a venting capacity. One drawback to the use of a drum-type dispensing system, however, is that the drum must be thoroughly cleaned and sterilized each time the drum is used or reused. As these drums are rather large, often having a 55 gallon or greater capacity, cleaning and sterilization equipment having an equally large capacity must be available on site. This cleaning and sterilization equipment often occupies valuable laboratory space and is costly to maintain and operate.

Drum-type dispensing systems often use fittings comprised of materials different than the barrel. These fittings often use threaded connections. During heating or cooling, the disparity in the rates of expansion between the fitting and the barrel allows the media to migrate along the threads. This migration may lead to compromising the integrity of the barrel system. Contamination, therefore, can result due to exposure of the sterile fluids to the outside atmosphere through the threaded fittings inserted into the bung hole of the barrel.

To assist in the mixing of cell culture media constituents, fittings may also be thermally or chemically bonded into holes formed in the sides of the barrel. These fittings are capable of accepting tubes which then extend from or depend into the barrel. For example, in the embodiment illustrated in FIG. 1, a top fitting 10 and a side fitting 12 are shown mounted in holes formed in a barrel 14. A section of tubing 16 extends from top fitting 10 to side fitting 12. Liquid cell culture media or the constituents of powdered cell culture media are introduced into the inside of barrel 14 through top fitting 10. The fluid inside barrel 14 is withdrawn through side fitting 12 and is pumped by a pump 18 back into top fitting 10, thereby creating a current useful in mixing the constituents of the cell culture media.

Another technique utilized for mixing the constituents of cell culture media is to withdraw air through top fitting 10 and force that air through the use of pump 18 through tubing 16 back into the barrel 14 through side fitting 12. As the air bubbles rise up through the liquid cell culture media contained within barrel 14, a mixing action is imparted and the powdered constituents of cell culture media will be mixed with the liquid constituents thereof.

It will be appreciated that the materials from which barrel 14 are comprised must be sufficiently strong to withstand the outward force of the liquids contained therein. In addition, the materials of barrel 14 must be compatible with the various methods of sterilization which the system must undergo. As the cell culture media must be thoroughly sterilized prior to introduction into the bioreactor, stringent techniques must be employed to assure that this sterility is maintained.

Users of the embodiment illustrated in FIG. 1 must either begin with a sterile barrel and utilize sterile techniques for introducing the cell culture media into that barrel, or must mix powdered cell culture media in the barrel and then sterilize the cell culture media prior to storage in another barrel. Even if the cell culture media is sterilized prior to introduction into a separate sterile storage barrel, some constituents may need to be added after the sterilization process.

The connections by which the tubing 16 is attached to fittings 10 and 12 must be disconnected if additional constituents are required. As a result, the contents of the barrel may be exposed to the outside atmosphere during the addition of these constituents.

For a more detailed discussion of the inherent weaknesses of the fitting used in the embodiment illustrated in FIG. 1, reference should now be made to FIG. 2, wherein a prior art fitting like top fitting 10 is illustrated. Top fitting 10 utilizes an attachment flange 20 which is chemically or thermally bonded to the sides or top of the barrel. An interior flange 22 provides support from the inside of the barrel. Protruding upward from attachment flange 20 is a sidewall 24. Sidewall 24 has internal threads 26 which interact with external threads 28 on a plug 30. Plug 30 cooperates with top fitting 10 to seal the contents of barrel 14.

To assist in forming a more perfect seal, a rubber washer 32 abuts a shoulder formed near the top of plug 30. Even with the use of rubber washer 32, however, the sealing system utilized in top fitting 10 is not perfect. Contamination can be introduced into the contents of barrel 14 through the threaded connection due to improper threading of plug 30 into top fitting 10 or due to manufacturing defects in the threads themselves.

A further contamination hazard resulting from the use of a fitting such as top fitting 10 occurs when tubing having a diameter inappropriate for use with a tubing connector 34 is utilized. Tubing having a variety of diameters is utilized in the industry and the appropriate tubing to be used with the various bioreactors and other peripheral devices is not always capable of determination prior to manufacture and shipping of the barrel. As a result, users are often tempted to force tubing having an improper diameter over barbed tubing connector 34. This can result in contamination entering barrel 14 or may even result in failure of the tubing.

In light of the foregoing, therefore, it would be an advancement in the art to provide apparatus and methods for the storing, reconstituting, dispensing and harvesting of cell culture media which do not require a user to have tubing which corresponds in size with the single tubing connector volume with the barrel.

It would be another advancement in the art to provide apparatus and methods for the storing, reconstituting, dispensing, and harvesting of cell culture media which do not utilize ports having threaded connections.

It would be a further advancement of the art to provide apparatus and methods for the storing, reconstituting, dispensing, and harvesting of cell culture media which would eliminate the need for a side entry to the barrel.

It would be a still further advancement in the art to provide apparatus and methods for the storing, reconstituting, dispensing, and harvesting of cell culture media which provide for access from the top of a cell culture media storage barrel to the contents of the bottom of the barrel.

OBJECTS AND BRIEF SUMMARY OF THE INVENTION

The present invention seeks to resolve problems incident to the apparatus and methods for the storing, reconstituting, dispensing and harvesting of liquid cell culture media, specifically, the apparatus of the present invention constitutes an important advancement in the art of reconstituting and especially dispensing cell culture media.

One object of the present invention is to provide for apparatus and methods for the storing, reconstituting, dispensing and harvesting of liquid cell culture media which do not require the user to have tubing which corresponds in size with the single tubing connector volume with a barrel.

Another object of the present invention is to provide apparatus and methods for the storing, reconstituting, dispensing, and harvesting of cell culture media which do not utilize ports having threaded connections.

A further object of the present invention is to provide apparatus and methods for the storing, reconstituting, dispensing, and harvesting of cell culture media which nave ports which eliminate the need for a side entry to the barrel.

A still further object of the present invention is to provide apparatus and methods for the storing, reconstituting, dispensing, and harvesting of cell culture media which provide access from the top of a cell culture media storage barrel to the contents of the bottom of the barrel.

Additional objects and advantages of the invention will be set forth in the description which follows or may be learned by the practice of the invention. The objects and advantages of the invention may be realized and obtained by means of the instruments and combinations particularly pointed out in the specification, drawings and dependent claims.

To achieve the forgoing objects and in accordance with the invention as embodied and broadly described herein, a port is provided for use in a system for storing, reconstituting, dispensing and harvesting cell culture media. One preferred embodiment of the present port invention is utilized in a system having an outer storage bag and an inner mixing bag. The mixing chamber formed within the mixing bag is capable of being placed in communication with one or more storage chambers formed in the storage bag. The mixing bag resides substantially within the storage chamber and is adapted to receive powdered cell culture media and other constituents therein. The mixing bag is also adapted to receive liquid cell culture media. When using powdered cell culture media, the powdered cell culture media is created by the introduction of both powdered and liquid constituents into the mixing chamber through an access port. Liquid cell culture media may be directly introduced into the storage chamber if sterile.

Between the mixing chamber and storage chamber, a pump may be located which acts to transport the reconstituted cell culture media from the mixing chamber to the storage chamber through a tubing system located therebetween. The cell culture media is sterilized as it passes between the pump and the storage chamber. Thereafter, the media in the storage chamber may be either stored or immediately dispensed therefrom into a cell bioreactor.

To access the storage chamber, one port is affixed through a wall of the storage bag. A similar port is affixed through the walls of both the mixing bag and the storage bag for use in the introduction of materials into the mixing chamber of the mixing bag. A tubing system may be attached to barbed tubing connectors affixed within apertures formed through the ports allowing communication therethrough to the respective chambers therein.

The preferred embodiment of the present invention comprises a port body having a mounting flange and upstanding walls to which a mounting base is attached. Apertures are formed through the mounting base in which barbed tubing connectors are affixed. The barbed tubing connectors are so sized so as to provide a variety of attachment points for tubing used in various configurations as required by different systems.

For example, when cell culture media is dispensed through one of the ports, the cell culture media is withdrawn from the storage chamber through a diptube depending therein which is attached to an end of the barbed tubing connector which protrudes into the storage chamber from the mounting flange. A discharge tube is attached to the end of the same barbed tubing connector which protrudes outwardly from the mounting base.

One embodiment of the present invention is provided with channels formed on the lower side of the mounting flange through which liquid cell culture media may be withdrawn from the storage chamber even when the mounting flange is placed in full contact with the floor of the storage chamber. The barbed tubing connectors affixed in the apertures formed in the mounting base protrude into the storage chamber a distance less than the distance between the mounting flange and the mounting base. As a result, the opening in the barbed tubing connector is not obscured by the bottom of the storage chamber even when the mounting flange is in direct contact with the floor of the storage chamber.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

Figure 1:
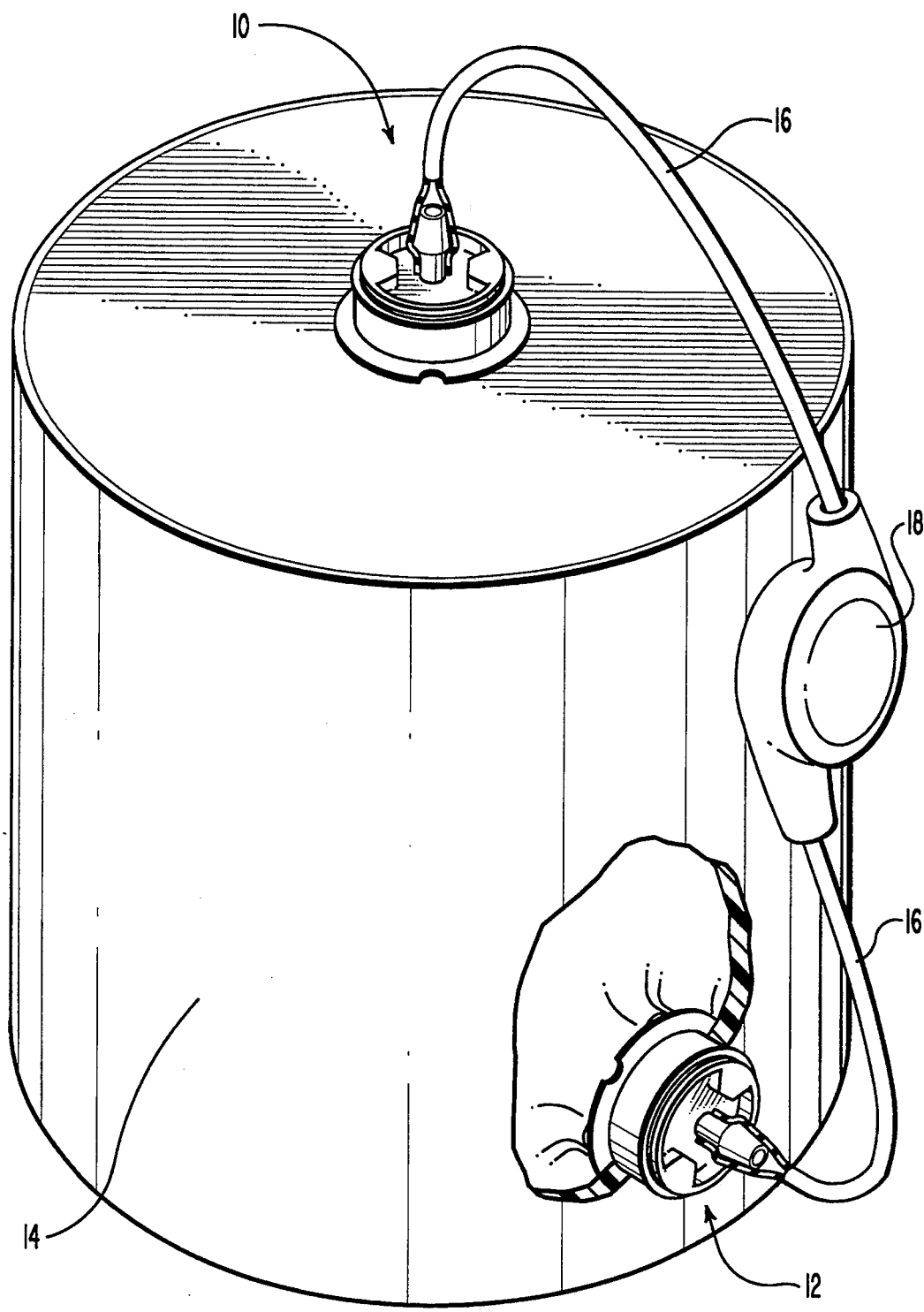
FIG. 1 is a perspective view of a barrel cell culture media system having portions cut-away to illustrate the mounting of access ports therein.
Figure 2:
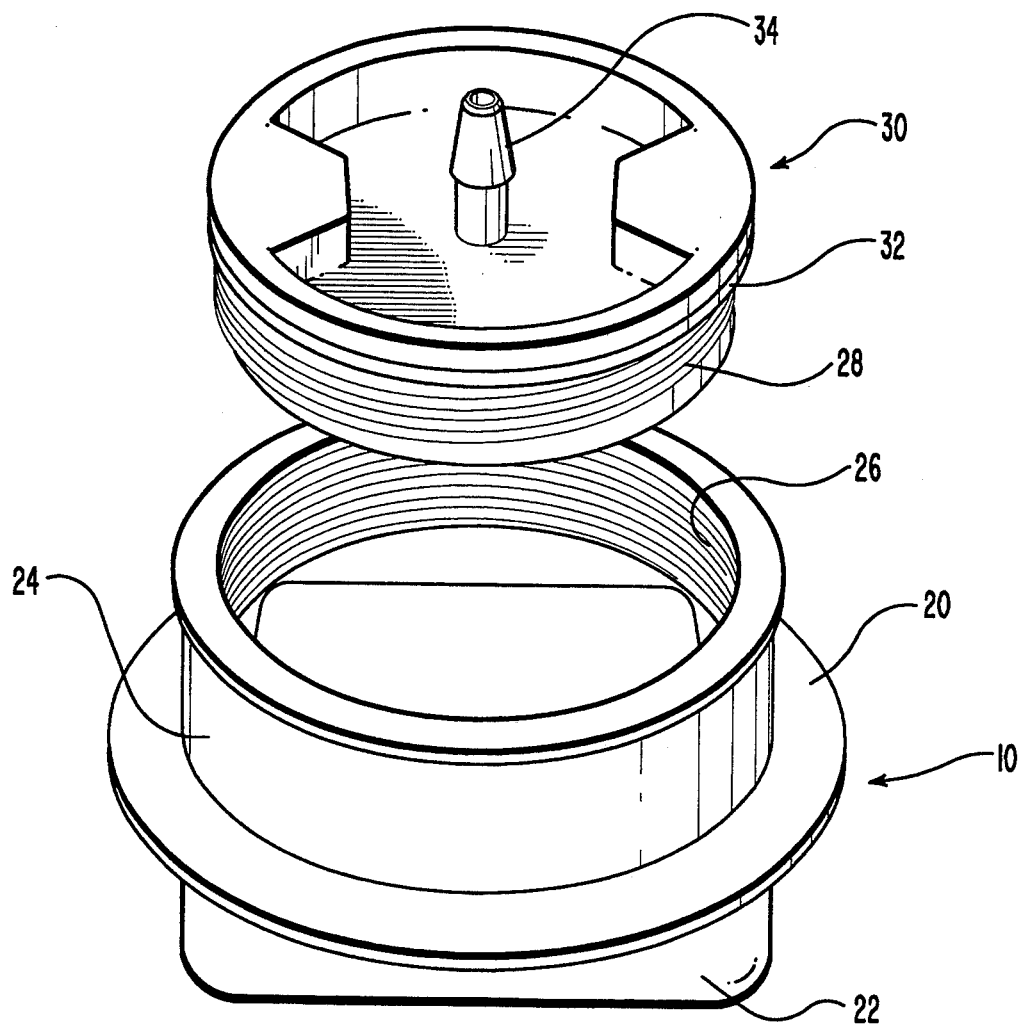
FIG. 2 is an exploded perspective view of a prior art access port such as that utilized in the embodiment illustrated in FIG. 1.
Figure 3:
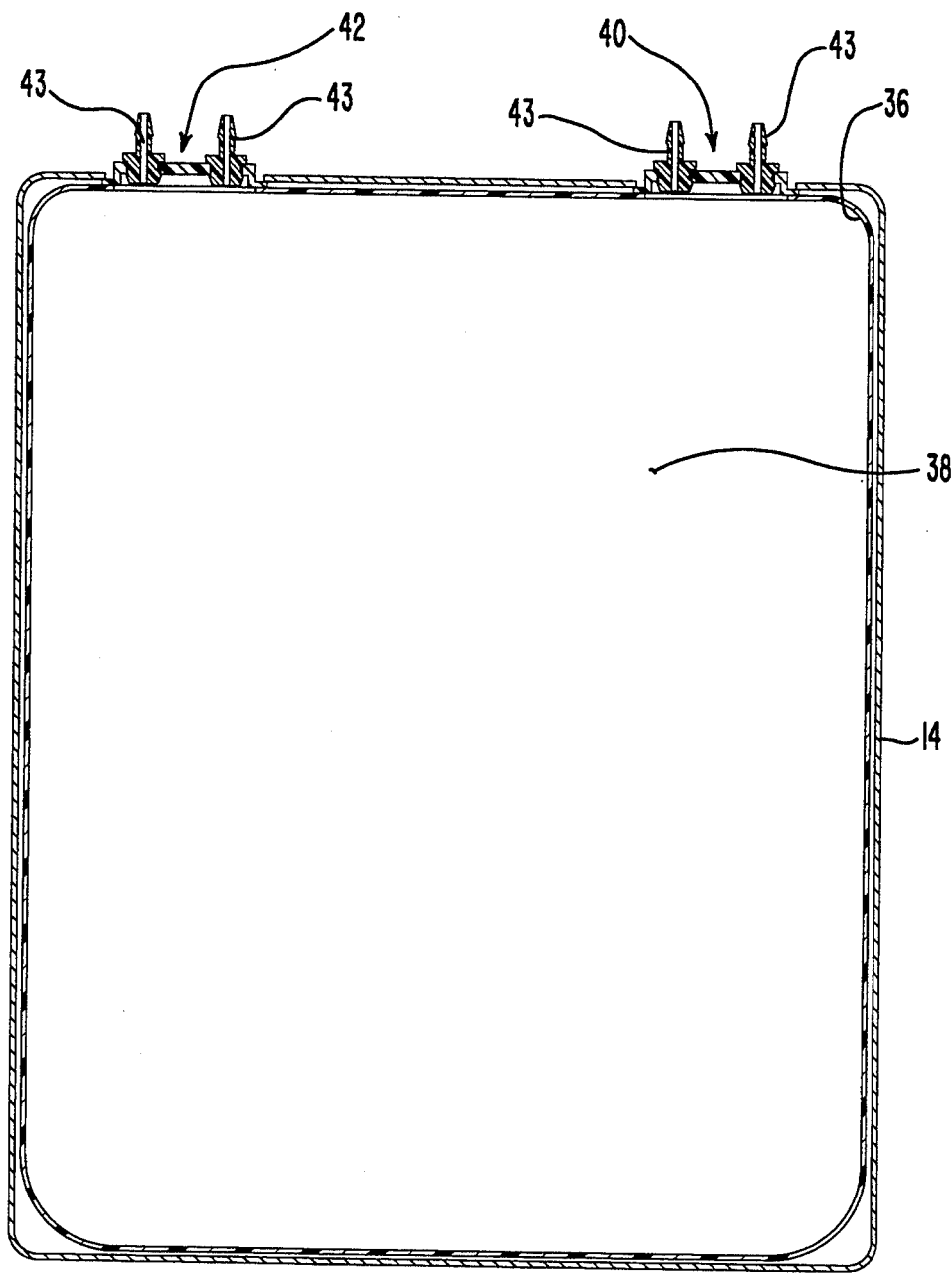
FIG. 3 is a cross-sectional elevation view of a cell culture containment system utilizing a bag supported by a barrel.

To overcome the sterilization problems associated with the use of a barrel type system, a system utilizing a plastic bag placed within the barrel has been developed. The barrel in these systems, serves only to support the bag and does not come into any direct contact with the sterile cell culture media. One example of the bag within a barrel type system is illustrated in FIG. 3. A barrel 14, similar to those barrels illustrated and utilized in other systems such as the system illustrated in FIG. 1, provide support to a bag 36 having a storage chamber 38 formed therein. Access to storage chamber 38 is achieved through a port 40. When cell culture media is to be dispensed, the media is withdrawn from storage chamber 38 through a diptube 41 and exits storage chamber 38 through a second port 42.

Figure 4:
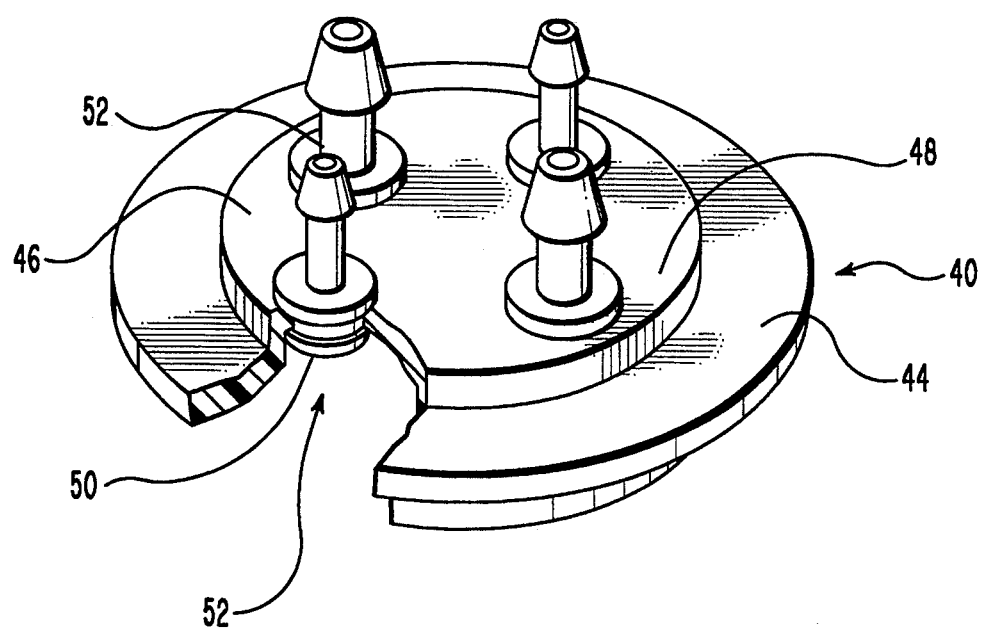
FIG. 4 is a partially cut-away perspective view of a port such as that used in the embodiment illustrated in FIG. 3.

Port 40 and port 42 are constructed in a nearly identical manner. The only difference between the two ports may be found in the size and configuration of fittings 43 affixed therein. Because port 42 is used to dispense cell culture media from storage chamber 38, the size and configuration of fittings 43 should conform to the tubing extending from port 42 to the bioreactor or another storage bag. The size and shape of the fittings used in port 40, however, should conform to the tubing used to introduce cell culture media into storage chamber 38. For a better understanding of the ports used in the cell culture media system illustrated in FIG. 3, reference should now be made to FIG. 4, wherein port 40 is illustrated in more detail.

To provide access to the contents of bag systems, fittings such as port 40 are thermally or chemically bonded into holes formed in the top or sides of the bag. These holes do not typically pass through the barrel. Port 40 is mounted in the hole in the bag at a mounting flange 44. A side wall 46 extends from mounting flange 44 to a fitting plate 48. An aperture 50 is formed in fitting plate 48 in which a barbed tubing connector 52 is mounted.

As liquid cell culture media within bag 36 is depleted, port 40 located on the top of the bag is compelled by gravity to approach the bottom of the bag. Two problems arise as port 40 approaches the bottom of the bag.

The first problem is that barbed tubing connectors 52, if no tubing is attached thereto, contact the bottom of the bag, and may bruise or puncture the bottom of the bag. The action of pumping cell culture media from the bag causes movement between the lower extremity of the barbed tubing connector and the inside of the bottom of the bag.

A second related problem is that as barbed tubing connectors 52 contact the bottom of the bag, they are often blocked by the bottom of the bag so that the fittings may no longer receive any of the liquid cell culture media contained within the bag. Suction produced by a pump located externally of the system, will continue to draw the bottom of the bag against the fitting and prevent further removal of any of the cell culture media from the bag. As a result, a significant portion of the liquid cell culture media may be discarded with the bag as this portion is inaccessible or efforts must be made to repeatedly reposition the bag within the barrel to obtain the remaining media.

Figure 5:
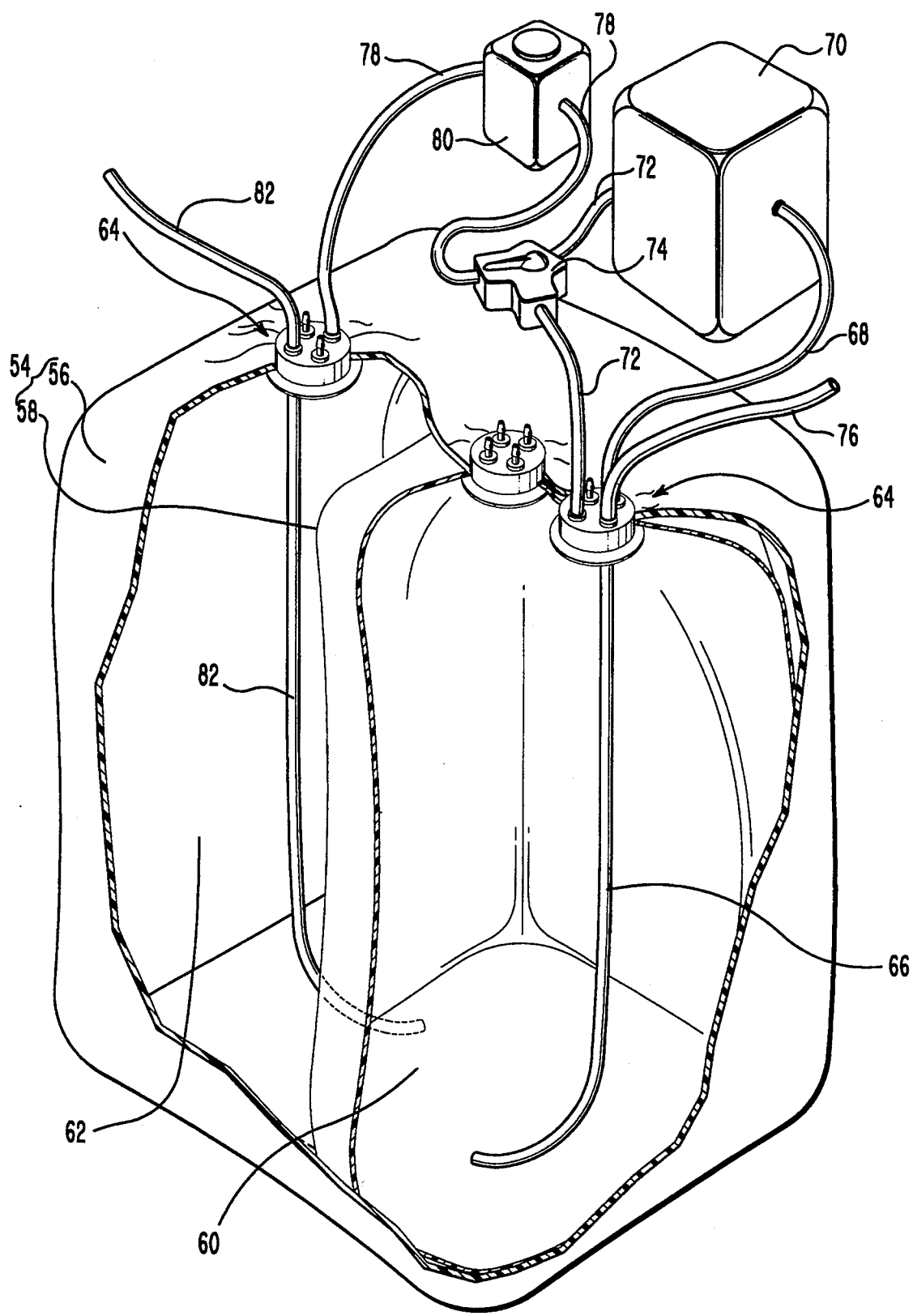
FIG. 5 is a partially cut-away perspective view of a cell culture containment system having a bag within a bag construction utilizing a preferred embodiment of the port of the present invention.

Referring now to FIG. 5, a bag within a bag containment system 54, is comprised of an outer bag 56 and an inner mixing bag 58. A mixing chamber 60 is formed within mixing bag 58. Likewise, a storage chamber 62 is formed within storage bag 56. Storage chamber 62 substantially envelopes mixing bag 58.

Although many materials may be employed for use in the construction of both the storage and mixing bags, any materials chosen should preferably be tested to assure that no reaction will occur with the media contained therein. The outer layer of the storage bag in the embodiment illustrated in FIG. 5 is constructed of EVA/Nylon/EVA or its functional equivalent. Mixing bag 58 is constructed of a plastic film which is preferably made of two layers of ultra low density polyethylene in which no slip additives or colorings have been introduced.

It is important that the materials selected for the walls of both the storage bag and the mixing bag have qualities which will not compromise the sterility of the media stored therein. By constructing the bags of two-layered material, additional strength and leak resistance are imparted to the containment system. Although the embodiment illustrated in FIG. 5 uses a two-layered material for construction of each bag wall, the present invention contemplates materials using one or many layers.

The presently preferred embodiments of the instant invention are utilized on systems having capacities from less than one liter to several thousand liters. In practice, the invention disclosed herein could be embodied in bags of any volumetric capacity. In addition to the concern for the reaction of the media with the materials of which the bags are constructed, a further consideration in the materials is the tolerance of the materials to the various forms of sterilization which may be applied to both the bag and the cell culture media contained therein. Thus, materials used in the construction of storage bag 56 and mixing bag 58 should be capable of withstanding radiation, ethylene oxide exposure or other known sterilization techniques.

Storage bag 56 is preferably manufactured from an extruded gusseted tube. One end of the gusseted tube has a thermal weld forming a bag having one open end. Likewise, mixing bag 58 is also formed from an extruded gusseted tube. Mixing bag 58 has one end thermally welded to form an open bag. Mixing bag 58 is inserted into storage bag 56 and both open ends are sealed with a common thermal weld thereby joining storage bag 56 to mixing bag 58 at the thermal weld.

At this point, mixing bag 12 is substantially enclosed within storage bag 10, both having a permanent contact between the bags only at the common thermal weld. After the manufacture of the bags, a port 64 is incorporated into the appropriate bags or combination of bags.

For example, the port incorporated in the bag for use in dispensing fluids therefrom may pass through only the top wall of storage bag 56. Any port providing access into mixing chamber 60, however, must pass through the walls of both storage bag 56 and mixing bag 58. To prevent binding and allow interaction between the two bags, port 64 is preferably located somewhere near the common thermal weld that seals and joins the two bags. If the port is used in a configuration wherein it need only pass through one bag, the port may be located wherever it functions most easily.

A rigid support barrel is used with this containment system to provide support to the sides of the bags when they are filled with liquid. It is preferred, therefore, that all ports be located at the top of the bag so as not to require any cutting in the barrel to provide access to the ports. Port 64 may function in a variety of manners. For example, port 64 may serve as an introduction port through which cell culture media may be introduced into mixing chamber 60.

In addition, port 64 may function to allow mixing of constituents within mixing chamber 60. To aid in the mixing action, media is withdrawn through a diptube 66 from mixing chamber 60 through tubing 68 and through a pump 70. Thereafter, the media is transferred through tubing 72 and may then "rain" back on the remaining constituents in mixing chamber 60 by once again passing through port 64.

The alternate method of mixing constituents in mixing chamber 60 employs the use of air contained within the headspace of mixing chamber 60 being withdrawn through tubing 72 and a valve 74 back through pump 70 and tubing 68 to be introduced into the bottom of mixing chamber 60 through diptube 66. The rising air bubbles serve to churn the contents within mixing chamber 60 and thereby mix the constituents placed therein.

Sampling of the contents of mixing chamber 60 may be accomplished through use of a sampling tube 76. Sampling tube 76 may also be attached to port 64 to structures which will be discussed in more detail later in the specification.

To convey cell culture media from mixing bag 58 into storage chamber 62, a series of tubes 78 and a filter 80 may be utilized. Pump 70, as used with this embodiment is a Cole Parmer peristaltic pump with a size 18 pump head. Other pumps may be used with equal or better flow rate with compatible tubing to fit the pump head. Pumps with lower flow capacity may require longer circulation than preferred for most applications. Pumps producing higher pressure may produce higher turbulence within the system.

To convey media from mixing chamber 60 to storage chamber 62, media is withdrawn through diptube 66 through tubing 68 and is pumped through pump 70 and valve 74 into tubing 78. Tubing 78 is attached to a filter 80 which sterilizes the cell culture media prior to introduction into the storage chamber. After sterilization, the media is conveyed through tube 78 and is introduced through another port 64 which is in communication with storage chamber 62. When the media is desired for use, the media may be dispensed through dispensing tube 82.

Although filter 80 is used to sterilize the media passing therethrough, it should be understood that other means of sterilization will be known to those skilled in the art such as gas sterilization, dry-heat, and steam. As sterilization is an evolving technology with constant improvements in equipment design and control, many sterilization techniques may be applied to the instant invention. Filter sterilization, however, is preferred in the present invention to prevent destruction of heat-labile medium components.

Most simple media for cultivation of bacteria can be autoclaved prior to use, but large volumes of media require longer periods of autoclaving. Vessels containing approximately 10 liters of liquid should be autoclaved at 123 degrees Celsius for 30–90 minutes depending upon the media constituents. Media containing solids may require up to 90 minutes for complete sterilization of a 10 liter volume. Unlike prior art systems wherein the entire barrel needed to be sterilized prior to use, the embodiment illustrated in FIG. 5 uses a bag which is sterilized at the factory prior to shipment.

As the media stored in the system illustrated in FIG. 5 is not placed in direct contact with the barrel, the barrel need not be sterilized prior to use. As a result, sterilization equipment having a much smaller capacity may be utilized. The equipment need only be capable of accommodating the deflated bag or the stream of media passing through the containment system. As all structures within the containment system depicted in FIG. 5 must be sterilization compatible, port 64 is preferably constructed of high-density polyethylene.

When media is withdrawn from mixing chamber 60 and is introduced into mixing chamber 62, the relative sizes of the bags will begin to change. When liquid is first introduced into mixing chamber 60, mixing bag 58 assumes the size and shape of the barrel in which it is placed. Thus, very little pressure is exerted on the seams located on the top and the bottom of the bag as most of the pressure is borne by the sides of the barrel. As fluid is pumped from mixing bag 58 into storage bag 56, storage bag 56 likewise assumes the size and shape of the mixing barrel while mixing bag 58 is reduced in size relative to storage bag 56.

Thus, although the overall size of the containment system remains the same, the relative size of the storage bag and the mixing bag will change during the conveyance of liquid media between mixing chamber 60 and storage chamber 62. As the pressure of the liquid outside of the mixing bag is substantially equivalent to the pressure inside the mixing bag during liquid media conveyance, there is almost no pressure on the seams of the mixing bag.

When most of the liquid media is conveyed from mixing chamber into storage chamber 62, the relative sizes of storage bag 56 and mixing bag 58 change so that mixing bag 58 is emptied and is substantially reduced in size.

When the liquid media is desired for use, the liquid media is withdrawn from storage chamber 62 through dispensing tube 82. Dispensing tube 82 is preferably of a size as to be easily accepted by the bioreactor into which the liquid media is introduced.

Figure 6:
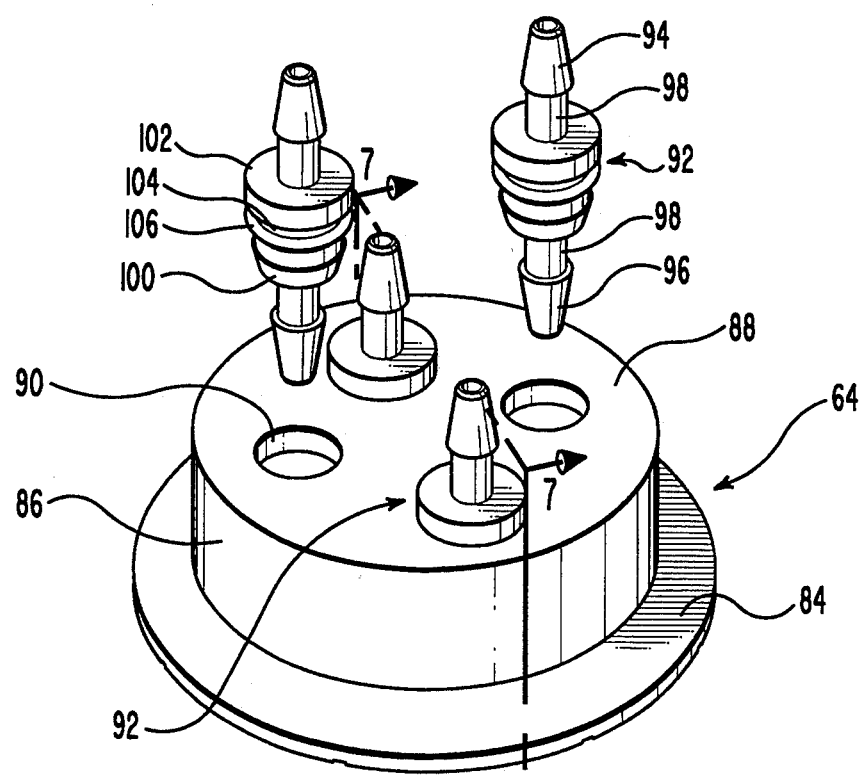
FIG. 6 is a partially exploded perspective view of a preferred embodiment of the present invention such as that utilized in the system illustrated in FIG. 5.

The features and structures of the inventive port may be more clearly understood by now referring to FIG. 6. FIG. 6 is a partially exploded perspective view of port 64. As discussed previously, port 64 is affixed into the top of the mixing bag through a hole which has been formed therein. A mounting flange 84 is thermally or chemically bonded to the bag surrounding the hole. A sidewall 86 extends upwardly from mounting flange 84 and terminates in access cap 88. Formed within access cap 88 are a plurality of apertures 90.

Apertures 90 are so shaped and configured so as to be capable of accepting a barbed tubing connector 92 therein. Barbed tubing connectors 92 each have an upper tip 94 and a lower tip 96 capable of accepting tubing. Upper tube 94 and lower tip 96 are beveled so as to form a barb at the termination of each end of a shaft 98.

Located approximately midway along the shaft 98 are a series of structures used in mounting a barbed tubing connector 92 in an aperture 90 formed in access cap 88. Barbed tubing connectors 92 are interference fitted into apertures 90 by forcing the barbed tubing connectors 92 through apertures 90 over a bevelled section 100 until the bottom of an abutment ring 102 abuts against the top of access cap 88. When mounted, the sides of aperture 90 form an interference fit with a sealing area 104 in which is located an O-ring 106.

Figure 7:
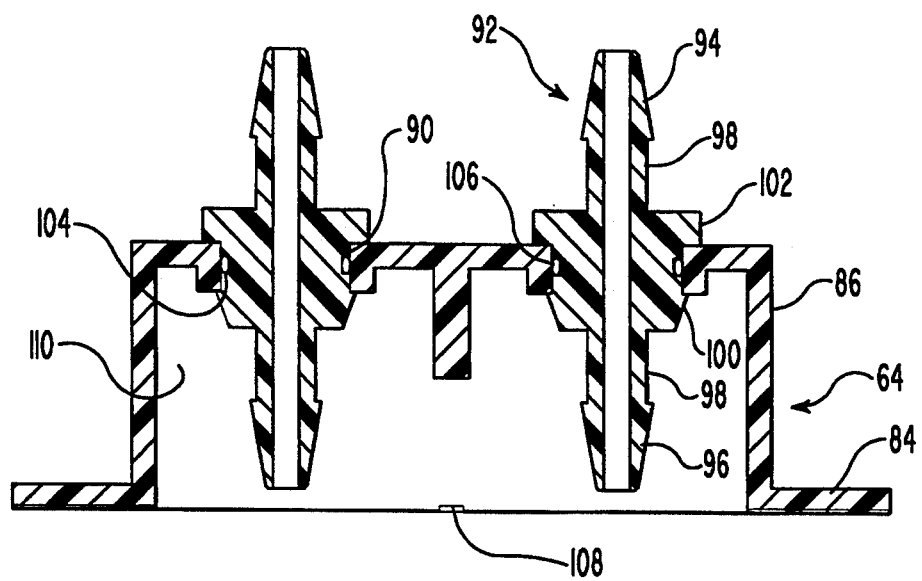
FIG. 7 is a cross-sectional view taken along lines 7—7 in FIG. 6.

Referring now to FIG. 7, the various structures of the barbed tubing connector and the interaction with port 64 can be better appreciated. As seen in FIG. 7, the sides of aperture 90 compress O-ring 106 in sealing area 104 to form an air and liquid tight seal around barbed tubing connector 92. Although the present invention contemplates using barbed tubing connectors capable of accommodating a variety of tubing sizes and requirements, sealing area 104 and O-ring 106 are identical in all of the barbed tubing connectors utilized in the present invention.

As a result, port 64 may be constructed and apertures 90 formed therein with universal applicability. The port may then be customized by insertion of barbed tubing connectors having upper tips 94 and lower tips corresponding in size to the requirements of the tubing anticipated to be attached thereto. This provides for a great diversity in the applications of port 64 and also allows the ports to be shipped in their generic form, having apertures 90 empty, along with a large selection of barbed tubing connectors so the end user may customize port 64 for any application on site.

Since port 64 is installed in the bag prior to shipment, this allows a generic bag and port combination to be shipped and then customized on site. The use of O-ring 106 in sealing area 104, prevents the introduction of contaminants around barbed tubing connector 94. This overcomes the disadvantages of the threaded connection used in prior art ports.

Sidewall 86 is constructed so as to have a height which is greater than the distance that lower tip 96 protrudes below access cap 88. As a result, lower tip 96 is always elevated above the bottom of the bag in a withdrawal area 110 even when mounting flange 84 is in full contact with the bottom of the bag. This allows media to be withdrawn from the bag even when the bag is fully collapsed. This ability to withdraw fluid even in a collapsed bag allows a substantial quantity of the fluid to be removed from the bag and reduces the amount of fluid wasted when the bag is discarded.

Figure 8:
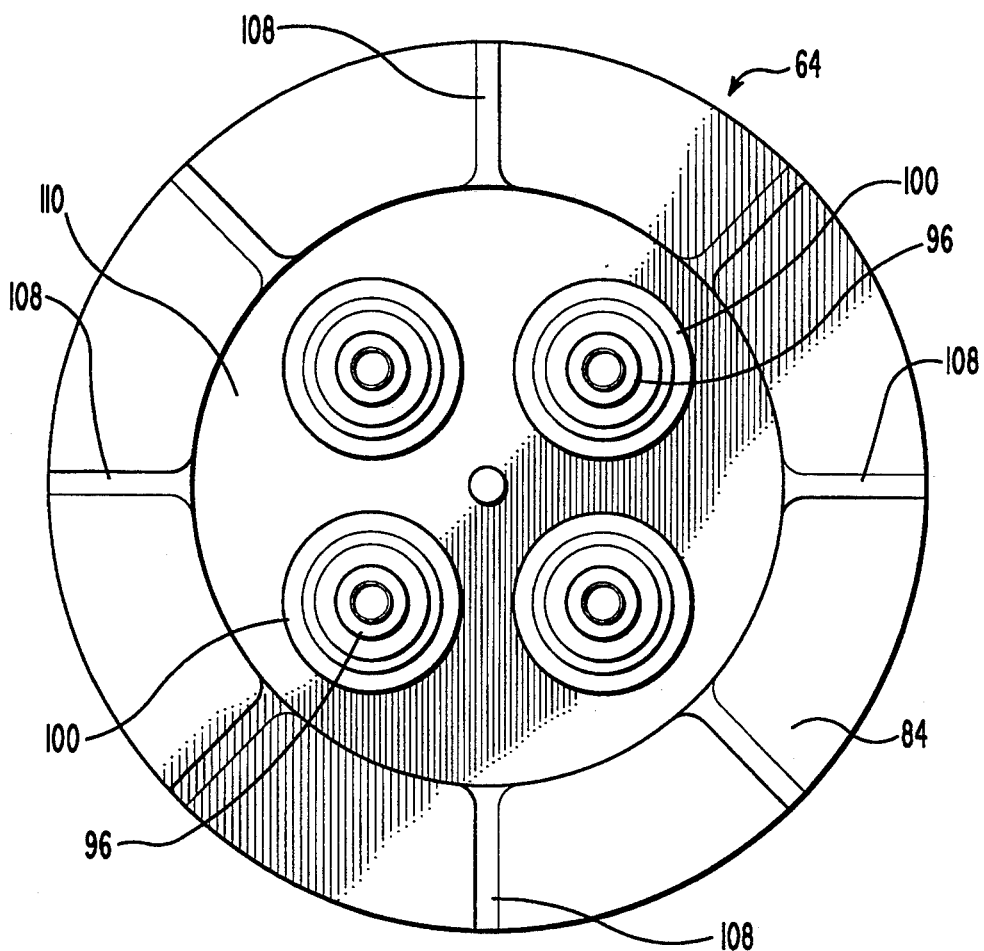
FIG. 8 is a plan view of the bottom of the embodiment of the present invention illustrated in FIGS. 6 and 7.

Referring now to both FIG. 7 and FIG. 8, the bottom of the embodiment illustrated in FIG. 7 is depicted. Formed within the bottom of mounting flange 84 are a series of channels 108 which communicate between the outside of port 64 into withdrawal area 110 inside of port 64. When mounting flange 84 is in contact with the bottom of the bag, channels 108 allow fluid to pass from outside of port 64 into withdrawal area 110. Suction provided by the pump through tubing connected to upper tip 94 produces a negative pressure within withdrawal area 110 thereby urging liquid to enter withdrawal area 110 and be conveyed through barbed tubing connector 92 out of the bag. Thus, by utilizing the instant invention, the majority of liquid in a cell culture storage bag may be removed without the need for frequently repositioning the bag or wasting much of the fluid contained therein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A multi-access port for use with a cell culture media containment system, the containment system utilizing a media bag having walls forming a chamber therein, the bags being supported within a barrel, the port comprising:
   a) a mounting flange having a top surface and bottom surface, the top surface being capable of affixation to the wall of the media bag surrounding a hole formed therein;
   b) an access cap;
   c) a sidewall extending from the mounting flange to the access cap;
   d) an aperture having walls formed through the access cap; and
   e) a tubing connector fitted into the aperture, the tubing connector having a lower tip extending below the access cap a distance less than the distance between the mounting flange and the access cap, and the tubing connector having an upper tip extending above the access cap.

2. A multi-access port as recited in claim 1, wherein the bottom surface of the mounting flange has formed therein a channel capable of providing liquid communication therethrough when the bottom surface of the mounting flange is covered.

3. A multi-access port as recited in claim 1, wherein the tubing connector has an upper tip and lower tip connected by a shaft, and wherein the tubing connector has a sealing structure located between the upper tip and the lower tip.

4. A multi-access port as recited in claim 3, wherein the sealing structure comprises:
   a) a beveled section easing introduction of the tubing connector into the aperture;
   b) a shoulder at the termination of the beveled section;
   c) an O-ring surrounding the shaft; and
   d) an abutment ring.

5. A multi-access port as recited in claim 4, wherein the abutment ring and the shoulder of the beveled section cooperate to prevent removal of the barbed tubing connector from the aperture.

6. A multi-access port as recited in claim 4, wherein the O-ring is located between the abutment ring and the beveled section.

7. A multi-access port as recited in claim 4, wherein the O-ring contacts the walls of the aperture to from an aseptic seal.

8. A multi-access port as recited in claim 1, wherein the mounting flange, access cap and sidewall are comprised of high density polyethylene.

9. A multi-access port as recited in claim 1, wherein the tubing connector has an upper tip having a diameter larger than the diameter of the lower tip.

10. A multi-access port as recited in claim 1, wherein the tubing connector has a lower tip having a diameter larger than the diameter of the upper tip.

11. A multi-access port as recited in claim 1, wherein the access cap has a plurality of apertures, each aperture having a tubing connector fitted therein having an upper tip with a diameter different than the diameters of the upper tips of the other tubing connectors.

* * * * *

UNITED STATES PATENT AND TRADEMARK OFFICE
CERTIFICATE OF CORRECTION

PATENT NO. : 5,350,080
DATED : September 27, 1994
INVENTOR(S) : Dennis Brown et al.

It is certified that error appears in the above-indentified patent and that said Letters Patent is hereby corrected as shown below:

Column 2, line 23, delete "and"

Column 2, line 43, "bung hole" should be --bunghole--

Column 4, line 32, "nave" should be --have--

Column 7, line 19, "envelopes" should be --envelops--

Signed and Sealed this

Eighteenth Day of April, 1995

*Attest:*

BRUCE LEHMAN

*Commissioner of Patents and Trademarks*

*Attesting Officer*